(12) United States Patent
Berger et al.

(10) Patent No.: US 8,075,500 B2
(45) Date of Patent: Dec. 13, 2011

(54) FETAL WELLBEING MONITORING APPARATUS AND PAD THEREFOR

(75) Inventors: Avraham Berger, Ramat Gan (IL); Avri Hazan, Givataim (IL); Michal Rinott, Tel Aviv (IL)

(73) Assignee: Biopad Ltd., Tel Aviv (IL)

( * ) Notice: Subject to any disclaimer, the term of this patent is extended or adjusted under 35 U.S.C. 154(b) by 212 days.

(21) Appl. No.: 12/452,670

(22) PCT Filed: Jul. 17, 2007

(86) PCT No.: PCT/IL2007/000894
§ 371 (c)(1),
(2), (4) Date: Jan. 14, 2010

(87) PCT Pub. No.: WO2008/010215
PCT Pub. Date: Jan. 24, 2008

(65) Prior Publication Data
US 2010/0191154 A1  Jul. 29, 2010

(51) Int. Cl.
*A61B 5/103* (2006.01)
(52) U.S. Cl. .................................... 600/591; 600/588
(58) Field of Classification Search .......... 600/588, 600/591
See application file for complete search history.

(56) References Cited

U.S. PATENT DOCUMENTS

| | | | |
|---|---|---|---|
| 3,187,098 A | 6/1965 | Farrar et al. | |
| 3,379,901 A | 4/1968 | Richards | |
| 3,488,821 A | 1/1970 | Richards | |
| 3,703,168 A | 11/1972 | Frink | |
| 3,763,851 A | 10/1973 | Haff et al. | |
| 3,913,563 A | 10/1975 | Ball | |
| 3,934,577 A | 1/1976 | Romani | |
| 3,989,034 A | 11/1976 | Hojaiban | |
| 4,143,650 A | 3/1979 | Hatke | |
| 4,493,043 A | 1/1985 | Forbath | |
| 4,711,585 A | 12/1987 | Fresquez et al. | |

(Continued)

FOREIGN PATENT DOCUMENTS

CN   1262918   8/2000
(Continued)

OTHER PUBLICATIONS

Measurement of Fetal Movements by Moving Coil Transducer by David Adler and Yona Mahler, IEEE Transactions of Biomedical Engineering, vol. BME-72, No. 12 Dec. 1980, pp. 738-740.

(Continued)

*Primary Examiner* — Max Hindenburg
*Assistant Examiner* — Emily Lloyd
(74) *Attorney, Agent, or Firm* — Abraham Hershkovitz; Harold L. Novick; Hershkovitz & Associates LLC (57) ABSTRACT

Fetal wellbeing monitoring apparatus including a generally flattened hemispherical housing and a turret-like user interface- having a user operated control panel for controlling operation of the fetal wellbeing monitoring apparatus and providing fetal wellbeing information to an expectant mother. Fetal wellbeing monitoring apparatus including a fetal motor activity sensor including a base plate with a base plate topside and a base plate underside with an elongated planar strain gauge film element defining a nominal measurement plane in a non-flexed state, and having a variable electrical property proportional to resilient elastic flexion in a transverse direction to the measurement plane on application of a bending moment and a fetal motor activity determination module for processing time varying information for determining fetal motor activity. Two-ply pad for use with the fetal wellbeing monitoring apparatus.

33 Claims, 11 Drawing Sheets

U.S. PATENT DOCUMENTS

| | | | |
|---|---|---|---|
| 4,781,200 | A | 11/1988 | Baker |
| 4,890,624 | A | 1/1990 | Ganguly et al. |
| 4,898,179 | A | 2/1990 | Sirota |
| 4,960,118 | A | 10/1990 | Pennock |
| D328,617 | S | 8/1992 | Emmel et al. |
| 5,140,992 | A | 8/1992 | Zuckerwar et al. |
| 5,265,619 | A | 11/1993 | Comby et al. |
| 5,609,156 | A | 3/1997 | Keith et al. |
| 5,817,035 | A | 10/1998 | Sullivan |
| 6,024,711 | A | 2/2000 | Lentle et al. |
| 6,045,500 | A | 4/2000 | Bieniarz |
| 6,135,969 | A | 10/2000 | Hale et al. |
| 6,206,821 | B1 | 3/2001 | Rhee |
| 6,275,719 | B1 | 8/2001 | Kandori et al. |
| 6,556,861 | B1 | 4/2003 | Prichep |
| 7,016,722 | B2 | 3/2006 | Prichep |
| D535,031 | S | 1/2007 | Barrett et al. |
| 7,296,733 | B2 | 11/2007 | Nguyen |
| 7,402,143 | B2 | 7/2008 | Berger et al. |
| D590,508 | S | 4/2009 | Tupin, Jr. |
| D599,909 | S | 9/2009 | Rinott et al. |
| 2003/0187370 | A1 | 10/2003 | Kodama |
| 2006/0058650 | A1 | 3/2006 | Sharony |
| 2006/0189882 | A1 | 8/2006 | Thomas |

FOREIGN PATENT DOCUMENTS

| | | |
|---|---|---|
| DE | 4225036 | 12/1993 |
| FR | 2602413 | 2/1988 |
| GB | 1348154 | 3/1974 |
| GB | 1369166 | 10/1974 |
| GB | 1398670 | 6/1975 |
| JP | 4309334 | 10/1992 |
| JP | 5000141 | 1/1993 |
| JP | 6296593 | 10/1994 |
| JP | 11089832 | 4/1999 |
| JP | 2002/034954 | 2/2002 |
| WO | WO 86/02250 | 4/1986 |
| WO | WO 89/04140 | 5/1989 |
| WO | WO 99/52020 | 10/1999 |
| WO | WO 2008/010216 | 1/2008 |

OTHER PUBLICATIONS

Fetal Movements in utero—A Review by E. Sadovsky, M.D. Department of Obsterics and Gynecology, Hadassah University Hospital, Jerusalem, Israel. vol. 3,No. 1,1992 pp. 27-36.

Classification of human fetal movement by Ilan Timor-Tritsch, M.D., Ivan Zador, M.Sc., Roger H. Hertz, M.D., Mortimer G. Rosen, M.D. Cleveland, Ohio. From the Department of Obstetrics and Gynecology, Cleveland Metropolitan General Hospital/Case Western Reserve University, School of Medicine. Received for publication Dec. 1, 1975, Revised Mar. 2, 1976, Accepted Mar. 18, 1976, pp. 70-77.

Mechanical reaction of the frontal abdominal wall to the impact load during gravidity by Karel Jelen & Antonin Dolezal* Charles University in Prague, Czech Republic, *General Teaching Hospital in Prague, Prof., MD J. Zivny. Submitted Oct. 20, 2002, accepted Nov. 9, 2002 pp. 15-20.

Recording of foetal movements: a comparison of three methods by L. Valentin, K. Marsal and K. Lindstrom University Hospital, Malmo, Sweden. Journal of Medical Engineering & Technology, vol. 10, No. 5 (Sep./Oct. 1986), pp. 239-247.

Human fetal respiratory movements: a technique for noninvasive monitoring with the use of a Tocodynamometer by Ilan E. Timor-Tritsch, Le-Roy J. Dierker, jr., Roger H. Hertz, Ivan Zador and Mortimer G. Rosen, Cleveland Metropolitan General Hospital, Cleveland. Ohio. Biol. Neonate 36: pp. 18-24 (1979).

Acoustic impedance of the maternal abdomen by George R. Wodicka, Alison M. Lam and Vinay Bhargava, Purdue University, Indiana 47907-1285. Journal of Acoustical Society of America, vol. 94, No. 1, Jul. 1993 pp. 13-18.

Differences in foetal heart rate variability from phonocardiography and abdominal electrocardiography by R. Ortiz, R. Gonzalez, M. A. Pena, S. Carrasco, M. J. Gaitan and C. Vargas. Universidad Autonoma Metropolitana-Iztapalapa, Mexico. Journal of Medical Engineering & Technology, vol. 26, No. 1, (Jan./Feb. 2002), pp. 39-45.

A comparison between maternal, tocodynamometric, and real-time ultrasonographic assessments of fetal movement by Y. Sorokin, M.D., S. Pillay, Ph.D., L.J. Dierker, M.D., R. H. Hertz, M.D., and M.G. Rosen, M.D. Am. J. Obstet. Gynecol. Jun. 15, 1981, vol. 140, No. 4, pp. 456-460.

Correlation between electromagnetic recording and maternal assessment of fetal movement by E. Sadovsky, W.Z. Polishuk, Y. Mahler and A. Malkin, at the Hadassah University Hospital, Jerusalem, Israel. Ref: The Lancet, May 26, 1973 pp. 1141-1142.

Maternal Perception, Tocodynamometric findings and real-time ultra-sound assessment of total fetal activity by W. Schmidt, I. Cseh, K. Hara and F. Kubli., Int. J. Gynaecol. Obstet., 1984, 22: 85-90.

Ultrasonic evaluation of fetal body movements over twenty-four hours in the human fetus at twenty-four to twenty-eight week's gestation by Constance Nasello-Paterson, BSc, Renato Natale, M.D., and Greg Connors, M.D., London, Ontario, Canada. Am J Obstet. Gynecol 1988 vol. 158 No. 2.

FETAL WELLBEING MONITORING APPARATUS AND PAD THEREFOR

CROSS-REFERENCE TO RELATED APPLICATIONS

This application is the National Phase filing of PCT application Serial Number PCT/IL2007/000894 filed 17 Jul. 2007, the entire contents of which are incorporated herein by reference.

FIELD OF THE INVENTION

The invention pertains to fetal wellbeing monitoring apparatus for providing fetal wellbeing information and pad therefor.

BACKGROUND OF THE INVENTION

Fetal motor activity has long been recognized as a good predictor of fetal wellbeing as discussed in Fetal Movements In utero—A Review, Sadovsky, E., M. D., Isr. J. Obstet. Gynecol. 1992: 3:27-36. Different types of fetal motor activity are discussed in an article entitled "Classification of human fetal movement" by Ilan Timor-Tritsch, et al., AM. J. Obstet. Gynecol., Volume 126, Number 1, pages 70-77, the contents of which are incorporated herein by reference. Exemplary fetal motor activity includes strong fetal kicks lasting from about ½ sec to about 1 sec, weak fetal punches lasting upto about ½ sec, and long fetal rolls lasting from about 10 sec to about 15 sec.

Commonly owned PCT/IL2003/000609 entitled Bio-filter Pad for Facilitating the Detection of an Occurrence of a Physiological Action, and Method Therefor, and Fetal Activity Monitoring Apparatus published under PCT International Publication No. WO 2004/012598 illustrates and describes fetal motor activity monitoring systems suitable for home use for providing information regarding fetal wellbeing based on detecting an expectant mother's abdominal movements as a consequence of fetal motor activity. WO 2004/012598's FIG. 1 shows a fetal motor activity monitoring system 1 including a bio-filter pad 2 adapted for removable intimate adhesion to an expectant mother's abdomen, and having a moving coil transducer 3 centrally disposed thereon for sensing her abdominal movements for providing a visual indication regarding a prevailing level of fetal motor activity. The transducer 3 is connected to a credit-card like, battery powered, fetal motor activity recorder 4 having an amplifier 6, an A/D converter 7, a signal processor 8, a memory 9, an output interface 11, for example, RS-232, and a fetal motor activity display 12 for comparing the prevailing fetal motor activity during a fetal motor activity monitoring session to a regular level of fetal motor activity determined on the basis of historical information. The fetal motor activity recorder 4 may be integrally formed with a transducer 3 together constituting fetal motor activity monitoring apparatus (see WO 2004/012598's page 5, lines 29-30). WO 2004/012598's FIG. 6 shows a fetal motor activity monitoring system 31 similar to the fetal motor activity monitoring system 1 except implemented for telemedicine purposes.

U.S. Pat. No. 4,898,179 to Sirota illustrates and describes a device for detecting, monitoring, displaying and recording of the heartbeats of a pregnant woman and her fetus. In addition, a third sensor can detect movement of the fetus and activate a display of a moving infant or a numerical display of the movement intensity or frequency.

U.S. Pat. No. 5,140,992 to Zuckerwar et al. illustrates and describes an ambulatory passive sensor for use in a fetal motor activity monitoring system. The passive sensor includes a piezoelectric polymer film combined with a metallic mounting plate fastened to a belt and electrically connected to a signal processing unit by means of a shielded cable. The sensor receives pressure pulses emitted from a fetus inside an expectant mother and has means for filtering out pressure pulses arising from other sources such as the maternal heart. The belt is resistant to stretching such that any pressure pulses cause compression of the piezoelectric polymer film thereby affecting its net polarization to produce detectable voltage changes.

SUMMARY OF THE INVENTION

The present invention is directed toward fetal wellbeing monitoring apparatus for determining fetal wellbeing and pad therefor. The fetal wellbeing monitoring apparatus includes a fetal motor activity sensor sensitive to naturally damped oscillations of transient abdominal displacements including shear waves of an expectant mother's abdomen due to her motor activity including breathing and her fetus' motor activity. Discussion regarding modes of movement of an expectant mother's abdomen can be found in an article entitled: "Mechanical reaction of the front abdominal wall to the impact load during gravidity", Karel Jelen & Antonin Dolezal, Neuroendocrinology Letters Nos. ½, February-April, Vol. 24, 2003, the contents of which are incorporated herein by reference. Different sections around an expectant mother's abdomen undergo different abdominal displacements in response to the same fetal motor activity, thereby leading to relative abdominal displacements between a pair of spaced apart contact points on her abdomen. The fetal wellbeing monitoring apparatus is preferably employed when an expectant mother is reclining for minimizing maternal motor activity except for her breathing, thereby facilitating detection of fetal motor activity.

Fetal motor activity sensors are preferably deployed to sense expectant mother's relative abdominal displacements along her abdomen's first mode of movement, namely, around her abdomen which demonstrates the largest abdominal movements for most major fetal movements. Alternatively, fetal motor activity sensors can be deployed to detect relative abdominal displacements along generally orthogonal first and second modes of movement. Clinical trials have shown that relative abdominal displacements along an expectant mother's abdomen's first mode of movement typically lie in the range from 0.005 mm to 0.05 mm depending on fetal age, type of fetal movement, and the like.

The fetal motor activity sensors employ a planar strain gauge film element defining a nominal measurement plane in a non-flexed state, and having a variable electrical property responsive to flexing in a transverse direction relative to their measurement planes on application of a bending moment. The fetal motor activity sensors are intended to be intimately juxtaposed against an expectant mother's abdomen such that her relative abdominal movements impart corresponding flexural movements in their strain gauge film elements in a transverse direction to their measurement planes for inducing time varying measurable changes in their electrical property. The strain gauge film elements are preferably of the piezoelectric type having a variable electrical charge as a function of flexing. However, other strain gauge technologies may be employed, for example, metallic foil arranged in a grid pattern, and the like.

Commercially available piezoelectric type strain gauge film elements typically demonstrate a linear mechano-electrical conversion of about 12 mV/micro strain where strain is defined as Δl/L where Δl represents deflection from their measurement planes, and L is their length. The strain gauge film elements are typically from about 10 mm to about 50 mm in length such that they develop an electrical signal in the order of at least several mVs on sensing small relative abdominal displacements up to about 100 mV on sensing large relative abdominal displacements approaching 0.03 mm. By virtue of the strength of this electrical signal, the fetal wellbeing monitoring apparatus requires an about 10 dB electrical signal amplification in contrast to the hitherto required 45±5 dB electrical signal amplification in the case of commonly owned WO2004/012598. Clinical trials have shown that strain gauge detection of relative abdominal displacements between spaced apart contact points on an expectant mother's abdomen is more efficacious for detecting fetal motor activity than the hitherto moving coil transducer approach.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE PRESENT INVENTION

FIGS. 1 to 7 show fetal wellbeing monitoring apparatus 10 dressed in a two-ply pad 80 for adhering to an expectant mother's abdomen for providing fetus wellbeing information to the expectant mother. The fetal wellbeing monitoring apparatus 10 includes a generally flattened hemispherical housing 11 made from rigid plastic material including a generally annular peripheral portion 12 including an upright sloping topside 13 and a generally annular flat underside 14, and a generally square shaped turret-like user interface 16 with a user operated control panel 17 raised with respect to the topside 13. The term "generally flattened hemispherical housing" in the context of the present invention is intended to encompass various shapes from truly hemispherical to oval shaped. The housing 11 and the pad 80 are preferably symmetrical about an axis of rotation A such that an expectant mother does not have to concern herself that she is correctly aligning the apparatus 10 when placing same on her abdomen.

The housing 11 includes a housing cover 18 including the upright sloping topside 13 and the turret-like user interface 16, and a housing base plate 19 constituting the generally flat underside 14 including a central sensor aperture 21 and six rounded protrusions 22. The housing base plate 19 is screwed to the underside of the housing cover 18 by a pair of screws 23. The turret-like user interface 16 includes a neck portion 24 and an uppermost surface 26 having a surround 27 flared with respect to the neck portion 24 whereby an expectant mother can readily grip the surround 27 for assisting in the manipulation of the apparatus 10. The uppermost surface 26 includes a generally square shaped light transmissive element 28 with an arrangement of recesses 29 for receiving a central display screen 31 and a peripheral arrangement of control buttons 32 including a Power Button 33, a Set Button 34, a Down Button 36 and an Up Button 37 constituting the control panel 17. The light transmissive element 28 is visible above the pad 80 along a first line of sight directed toward the user interface 16 from above and a second line of sight directed toward the user interface 16 from the side. The light transmissive element 28 is preferably formed from perspex, and the like.

Figure 1:
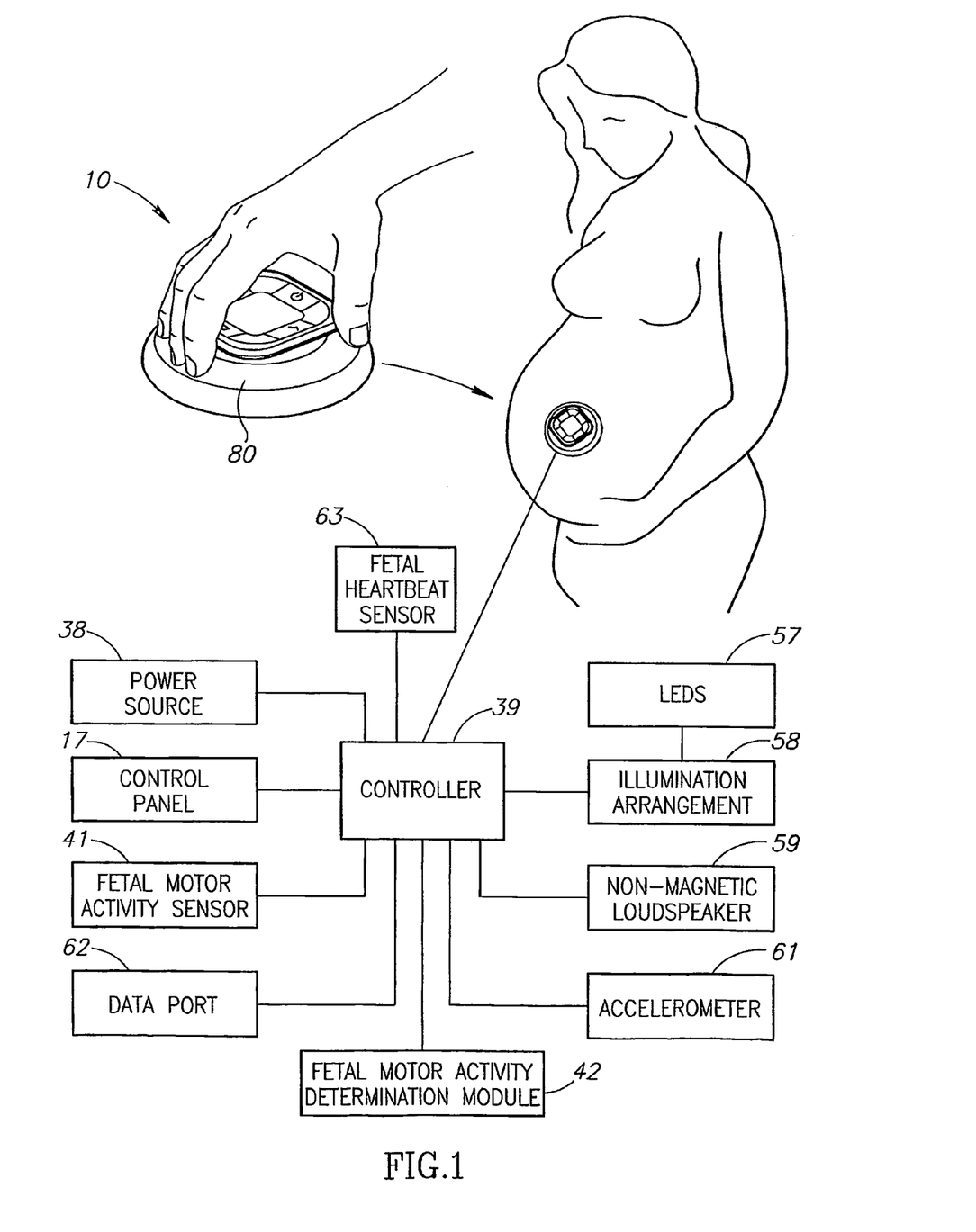
FIG. 1 is a combined pictorial representation of an expectant mother using fetal wellbeing monitoring apparatus dressed in a two-ply pad adhered to her abdomen for providing fetus wellbeing information and a block diagram of the fetal wellbeing monitoring apparatus.
Figure 2:
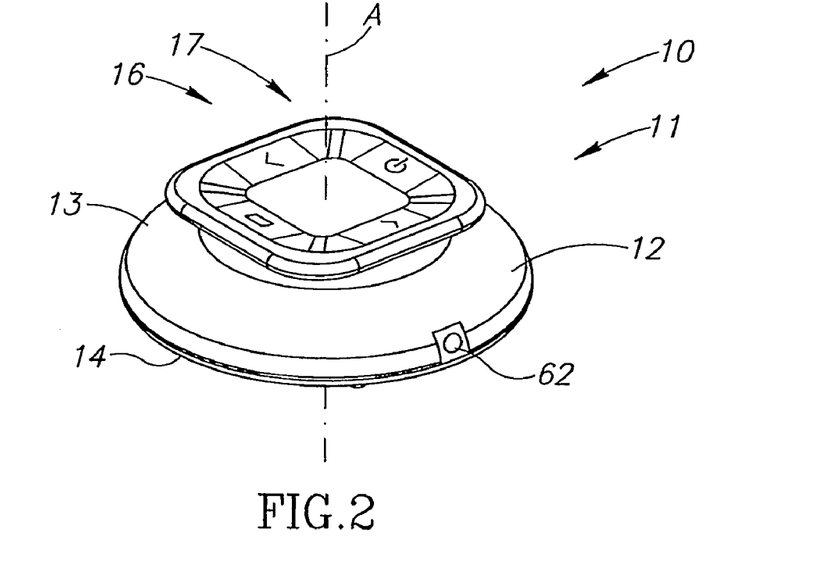
FIG. 2 is a perspective view of the fetal wellbeing monitoring apparatus.
Figure 3:
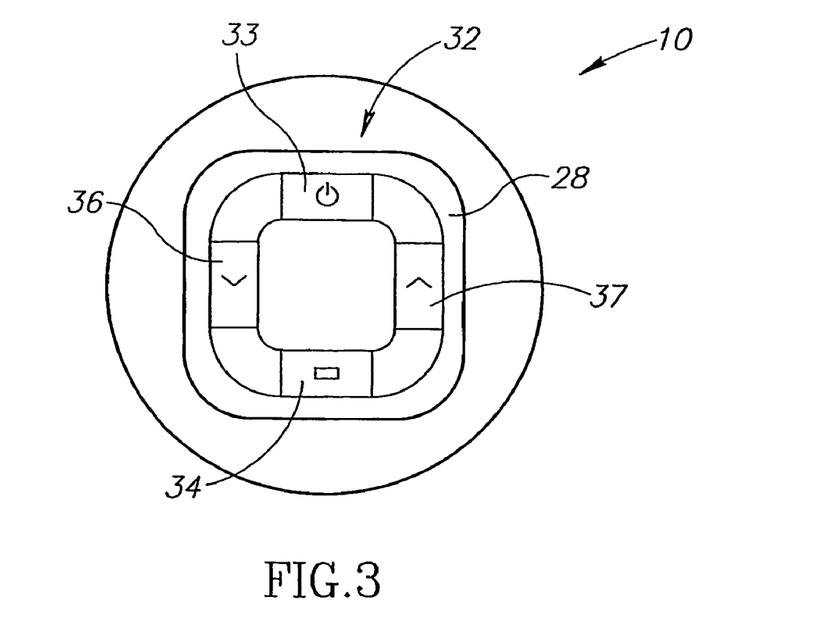
FIG. 3 is a top plan view of the fetal wellbeing monitoring apparatus.
Figure 4:
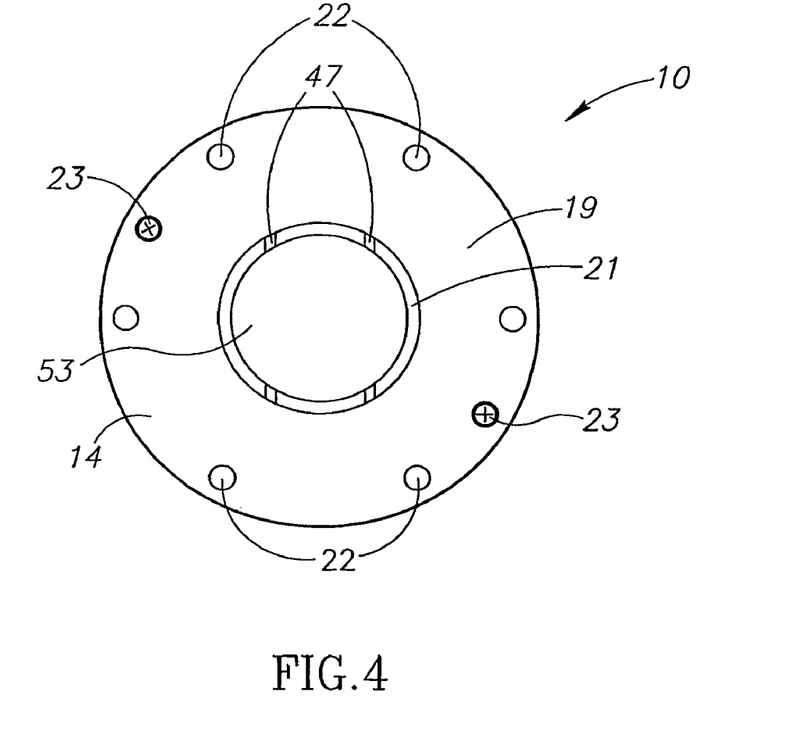
FIG. 4 is a bottom plan view of the fetal wellbeing monitoring apparatus.
Figure 5:
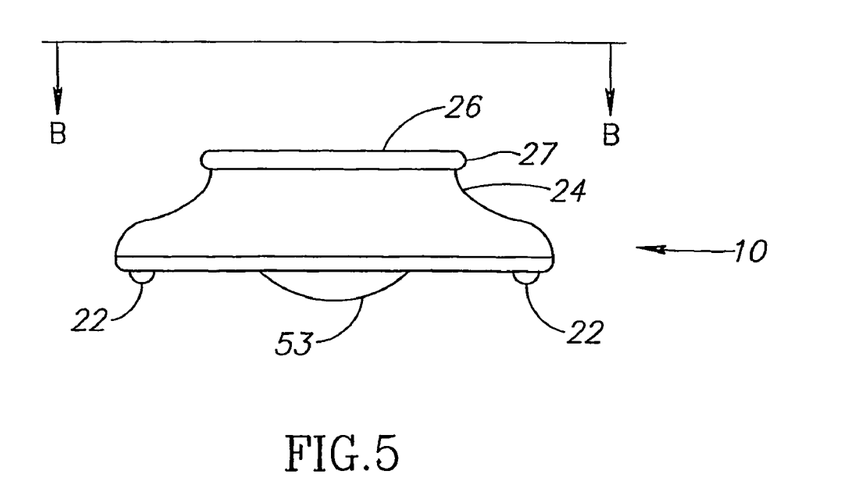
FIG. 5 is a side elevation view of the fetal wellbeing monitoring apparatus.
Figure 6:
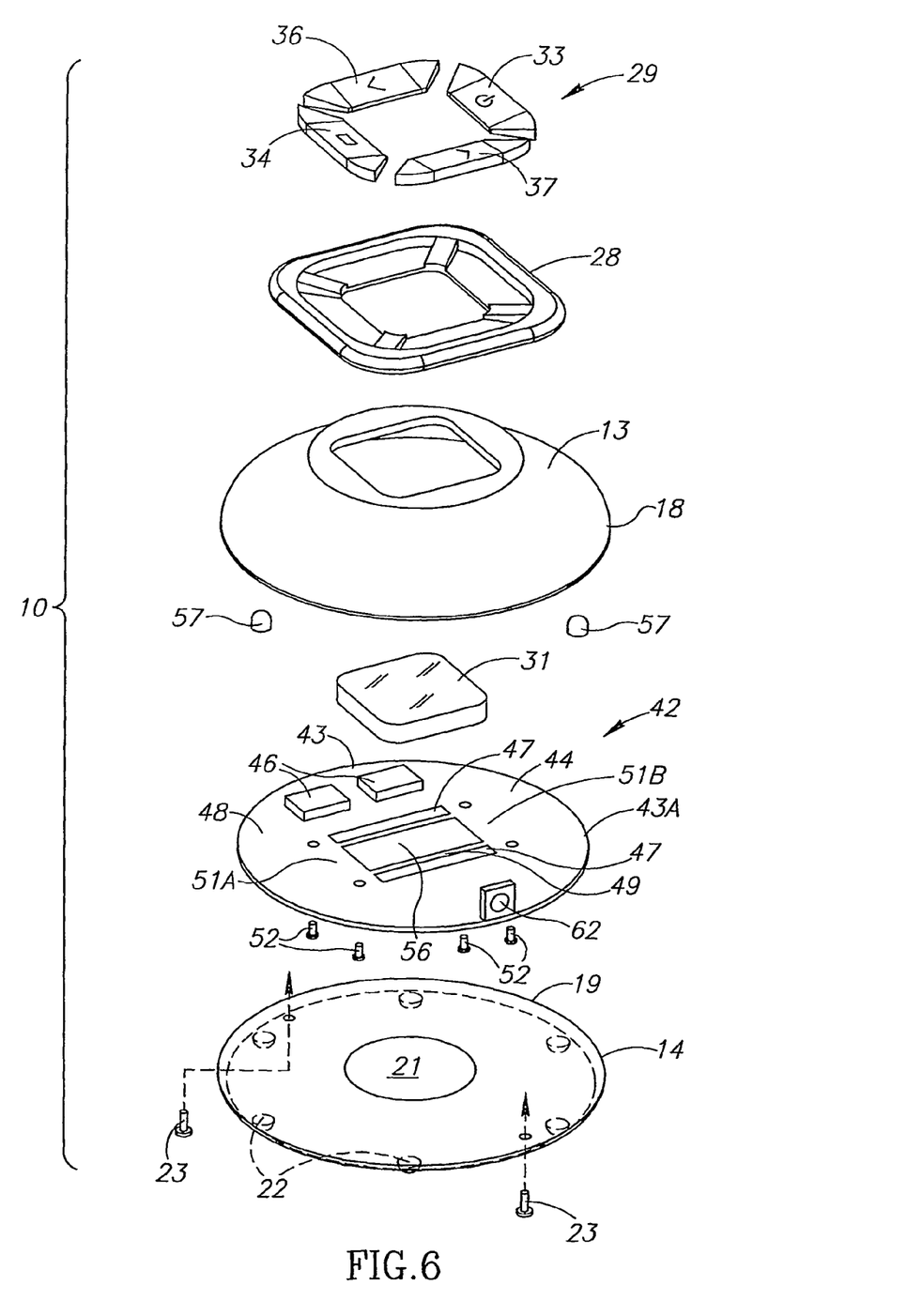
FIG. 6 is an exploded view of the fetal wellbeing monitoring apparatus.
Figure 7:
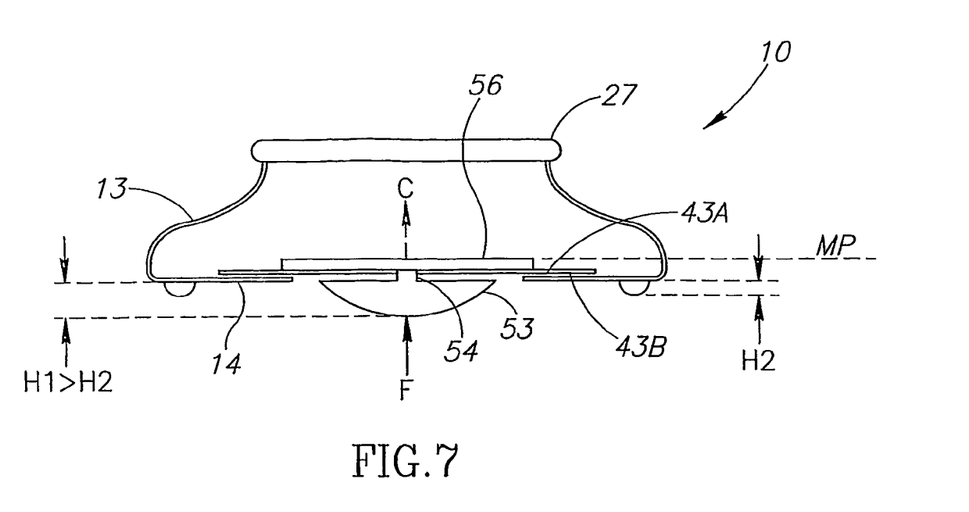
FIG. 7 is a cross section of the fetal wellbeing monitoring apparatus along line B-B in FIG. 5.

The fetal wellbeing monitoring apparatus 10 includes a power source 38 such as CR2 type 3V lithium batteries, a controller 39, a fetal motor activity sensor 41 for sensing fetal motor activity on intimate juxtaposing of the fetal wellbeing monitoring apparatus 10 against an expectant mother's abdomen, and a fetal motor activity determination module 42 including DSP capabilities for processing time varying information from the fetal motor activity sensor 41 for determining fetal motor activity inducing the transient abdominal movements sensed by the fetal motor activity sensor 41. The fetal motor activity determination module 42 includes memory for use as a data logger for inter alfa event data logging including event date, event time, event duration, event type, and the like. The fetal motor activity sensor 41 includes a base plate 43 having a base plate topside 43A and a base plate underside 43B. The base plate 43 is preferably formed from a resiliently flexible material, for example, metal, epoxy glass, plastic material, and the like, and is employed as a printed circuit board 44 including electronic components 46.

The base plate 43 includes a pair of opposite elongated weakened regions 47 for defining a major base plate surround 48 and a minor base plate beam 49 supported by a pair of generally opposite and parallel beam supports 51A and 51B for resilient elastic bowing with respect to the major base plate surround 48 on application of a force F thereagainst in a direction perpendicular to the major base plate surround 48 as shown by arrow C (see FIG. 7). The opposite elongated weakened regions 47 can be straight or arcuate and constituted by a pair of throughgoing slits, scored lines for locally reducing base plate thickness, and the like. The beam supports 51A and 51B are strengthened by two pairs of screws 52 employed for screwing the base plate 43 to the underside of the housing cover 18. The screws 52 are concealed by the housing base plate 19 on its screw attachment to the housing cover 18.

The minor base plate beam 49 rigidly supports a downward depending inverted mushroom shaped rounded contact 53 for protruding through the central sensor aperture 21 for indenting an expectant mother's abdomen. The rounded contact 53 has an external diameter of about 27 mm and is mounted on a stem 54 having a diameter of about 6 mm for concentrating strain acting upon the minor base plate beam 49 thereby maximizing its flexion due to abdominal displacements. The rounded contact 53 and the rounded protrusions 22 respectively define heights H1 and H2 relative to the housing base plate 19 where H1>H2. Typically, H1 is in the region of about 5 mm and H2 is in the region of 2-3 mm.

The minor base plate beam 49 is provided with an elongated generally rectangular planar strain gauge film element 56 deployed lengthwise therealong. The strain gauge film element 56 is preferably formed of piezoelectric material, for example, PolyVinylidine DiFluoride (PVDF), and the like. Suitable PVDF material is commercially available from Measurement Specialities, Inc. (MSI), USA, in a range of thicknesses from about 20 μm to about 100 μm. The strain gauge film element 56 defines a nominal measurement plane MP in its non-flexed state and has a variable electrical property proportional to resilient elastic flexion in a transverse direction to the measurement plane on application of a bending moment. The film element 56 is adhered to the resiliently flexible material by adhesive material such as VHB available from 3M, Inc., USA. The base plate 43 is raised above the housing base plate 19 by a separation of about 1 mm thereby affording thermal protection for the film element 56.

The controller 39 selectively illuminates one or more light sources 57, for example, LEDs, and the like, for illuminating the light transmissive element 28 thereby affording an illumination arrangement 58 for providing illumination responsive to fetal motor activity in terms of illumination intensity and illumination duration. Illumination intensity is preferably proportional to fetal motor activity such that greater the fetal motor activity greater the illumination intensity. Illumination duration is preferably proportional to the duration of a fetal motor activity such that the illumination arrangement 58 is illuminated longer during the course of a slow fetal roll as opposed to a sharp fetal kick. Moreover, the illumination arrangement 58 can provide low level illumination in the case of uncertainty whether a detected abdomen movement is due to an expectant mother's movement or fetal motor activity.

The controller 39 operates a non-magnetic loudspeaker 59 for issuing a first set of operation sounds regarding operation of the fetal wellbeing monitoring apparatus 10 and a second set of movement sounds different therefrom and responsive to fetal motor activity. Suitable non-magnetic loudspeakers include inter alia piezoelectric loudspeakers, for example, CUI Inc.'s Part No. CMT-1603 commercially available from CUI, Inc., Tualatin, Oreg. 97062, USA.

The fetal wellbeing monitoring apparatus 10 includes a maternal body movement detection module 61 for detecting maternal body movements which hinder monitoring fetal motor activity for preferably issuing audible warnings on detection of same. Such maternal body movements include sudden bodily movements, coughing, and the like. Suitable maternal body movement detection modules 61 can include an accelerometer, for example, ST Part No. LIS 3 L 02, and the like.

The fetal wellbeing monitoring apparatus 10 can be optionally provided with a data port 62 for enabling I/O operations with external devices. The data port 62 can be any standard I/O port including inter alia RS-232, USB, and the like.

The fetal wellbeing monitoring apparatus 10 can be optionally provided with a passive fetal heartbeat sensor 63 for detecting fetal heartbeat for enabling a non-stress test of fetal wellbeing. Suitable passive fetal heartbeat sensors 63 include inter alia a piezoelectric sensor, a bio-impedance sensor, an IR sensor, and the like.

Figure 8:
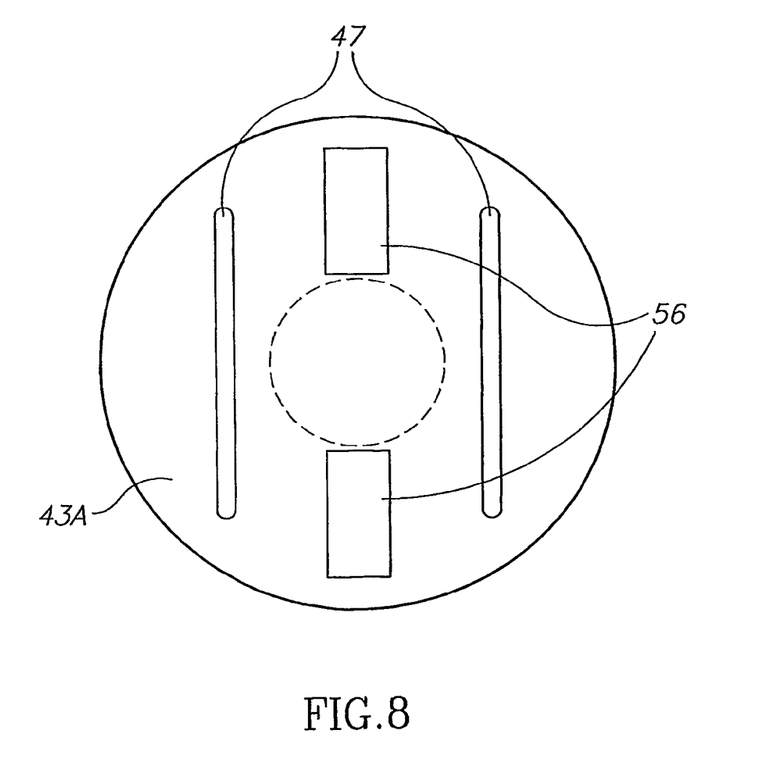
FIG. 8 is a top plan view of a fetal motor activity sensor including a pair of spaced apart strain gauge film elements.

FIG. 8 shows the base plate topside 43A can be provided with a pair of spaced apart elongated planar strain gauge film elements 56 as opposed to a single strain gauge film element for providing phase information which can be employed for providing information including inter alia the direction of travel of an abdominal displacement, the speed of propagation of a shear wave traveling along an expectant mother's abdomen, and the like.

Figure 9:
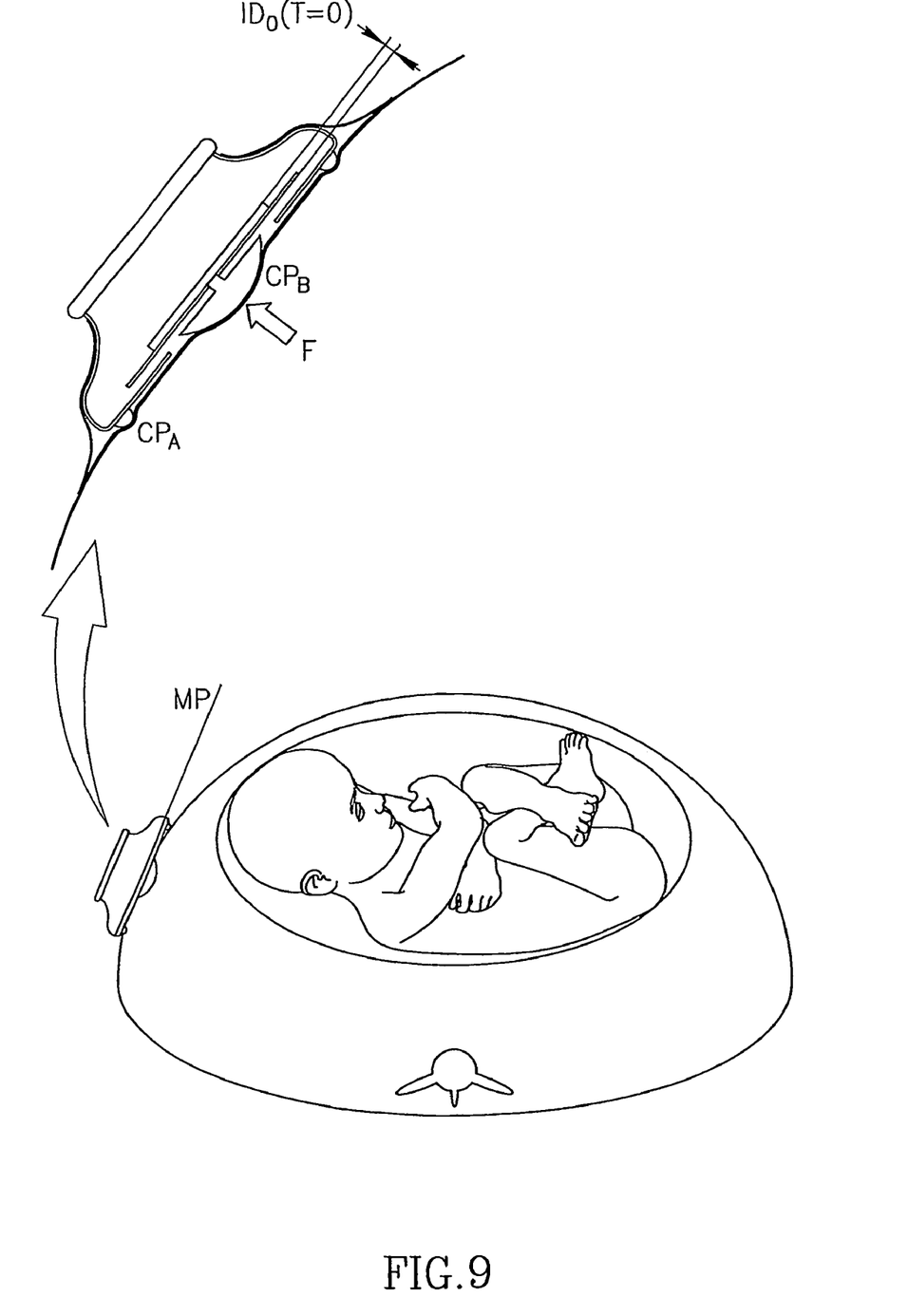
FIG. 9 is a schematic near transverse cross section of an expectant mother's abdomen prior to fetal motor activity including a close-up view for showing an initial state of the fetal wellbeing monitoring apparatus with respect to her abdomen.
Figure 10:
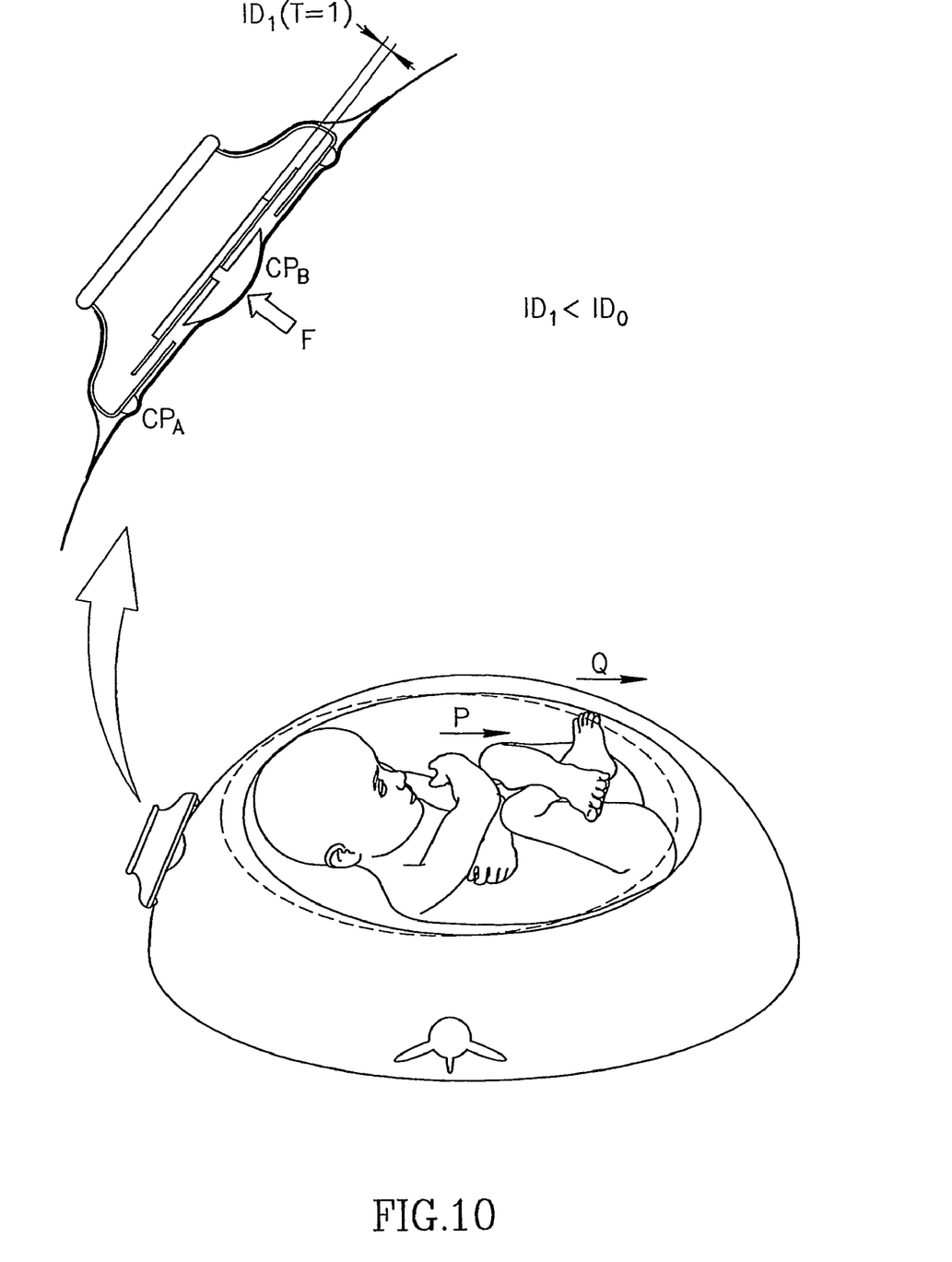
FIG. 10 is a schematic near transverse cross section of an expectant mother's abdomen immediately after a strong fetal kick urging her abdomen to the right including a close-up view for showing a subsequent state of the fetal wellbeing monitoring apparatus with respect to her abdomen.
Figure 11:
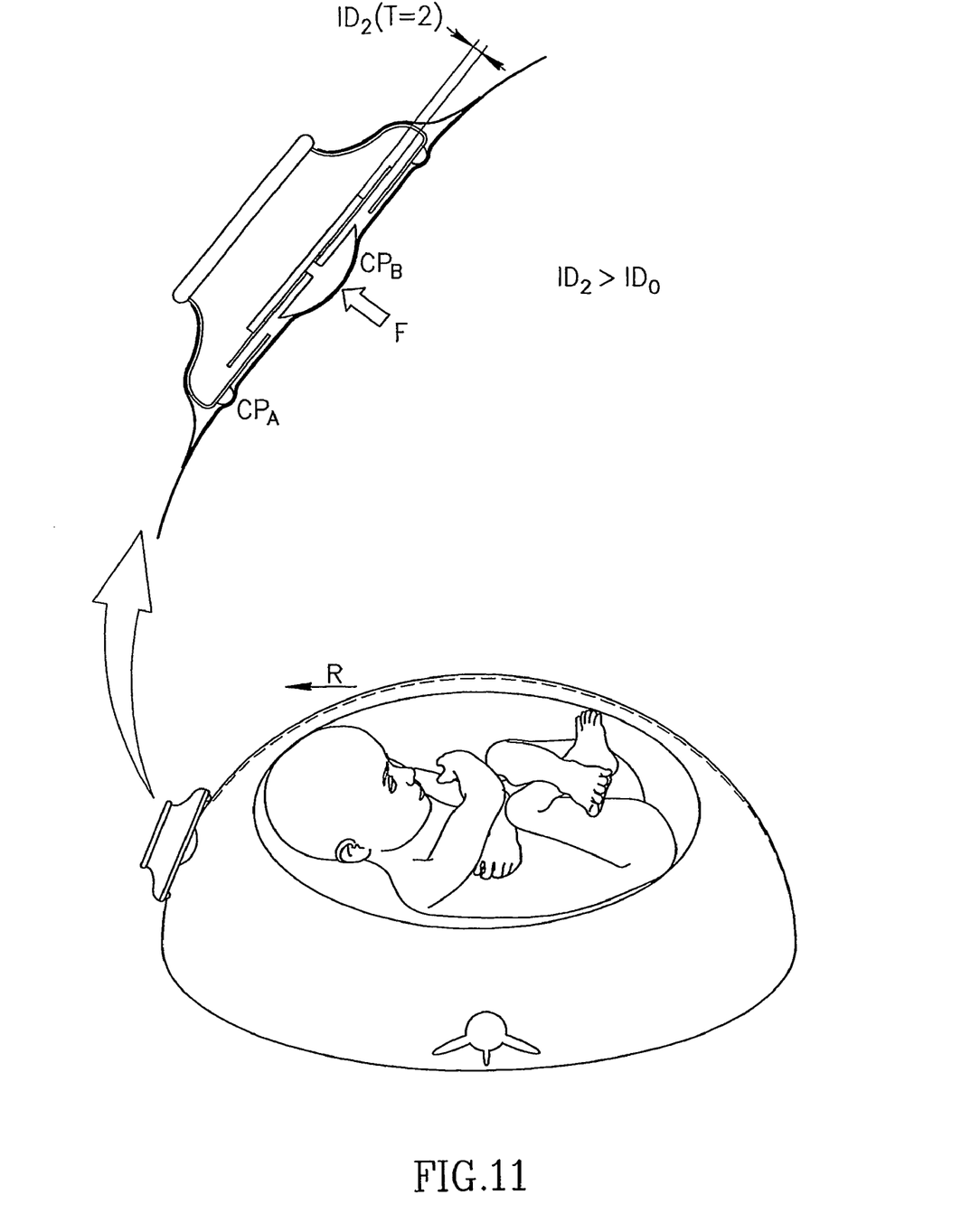
FIG. 11 is a schematic near transverse cross section of an expectant mother's abdomen on its return oscillation towards the left including a close-up view for showing a further subsequent state of the fetal wellbeing monitoring apparatus with respect to her abdomen.

FIGS. 9 to 11 are schematic transverse cross sections of an expectant mother's abdomen for illustrating operation of the fetal wellbeing monitoring apparatus 10 for providing time varying information consequent to a single strong fetal kick to the right.

FIG. 9 shows the fetal wellbeing monitoring apparatus 10 intimately juxtaposed against an expectant mother's abdomen such that its most posterior located rounded protrusion 22 slightly indents her abdomen at a first contact point $CP_A$, its protruding contact 53 indents her abdomen at a contact point $CP_B$ spaced apart from the contact point $CP_A$, and its most anterior located rounded protrusion 22 less indents her abdomen, if at all. The degree of indentation of a fetal wellbeing monitoring apparatus 10's most anterior located rounded protrusion 22 into an expectant mother's abdomen depends on its location since her abdomen is straighter along its opposite sides and more rounded at the front depending on inter alia pregnancy week, and the like. The pad 80 intimately urged against an expectant mother's abdomen transfers the force F to urge the fetal motor activity sensor 41 into a nominal flexed state in the absence of fetal motor activity. Thus, the base plate beam 49 is outwardly flexed in a transverse direction which in turn outwardly flexes the strain gauge film element 56 relative to its nominal measurement plane MP by an indentation depth $ID_0$ (T=0) in the order of about 0.2 mm about 0.5 mm.

FIG. 10 shows how a strong fetal kick to the right denoted by arrow P initially urges the expectant mother's abdomen to the right denoted by arrow Q such that her abdomen assumes a new lateral position shown in solid lines relative to its initial position shown in dashed lines. The shifting of the expectant mother's abdomen to the right causes the contact point $CP_B$ to move to the right through a greater displacement than the contact point $CP_A$ thereby reducing the outward flexing of the fetal motor activity sensor 41 relative to its initial flexed state. Typically, the contact point $CP_A$ moves to the right from its initial position by about 0.01 mm÷0.02 mm whilst the contact point $CP_B$ moves to the right from its initial position by about 0.03 mm÷0.05 mm subsequent to a strong fetal kick to the right. Consequently, the protruding contact 53 indents less into the expectant mother's abdomen. The strain gauge film element 56 still remains outwardly flexed but to a lesser degree than in its initial flexed state, namely, $ID_1 < ID_0$.

FIG. 11 shows the damped oscillation of the expectant mother's abdomen to the left denoted by arrow R after the aforesaid strong fetal kick to the right to assume a new lateral position shown in solid lines relative to its initial position shown in dashed lines. The shifting of the expectant mother's abdomen to the left causes the contact point $CP_B$ to move more to the left than the contact point $CP_A$ thereby increasing the outward flexing of the fetal motor activity sensor 41 relative to its initial flexed state such that $ID_2 > ID_0$. The absolute increase in flexing of the fetal motor activity sensor 41 in the second oscillation is typically less than the absolute decrease in the first oscillation towards the right by virtue of dissipation of some of the energy transferred to the expectant mother's abdomen by the fetal kick.

Figure 12:
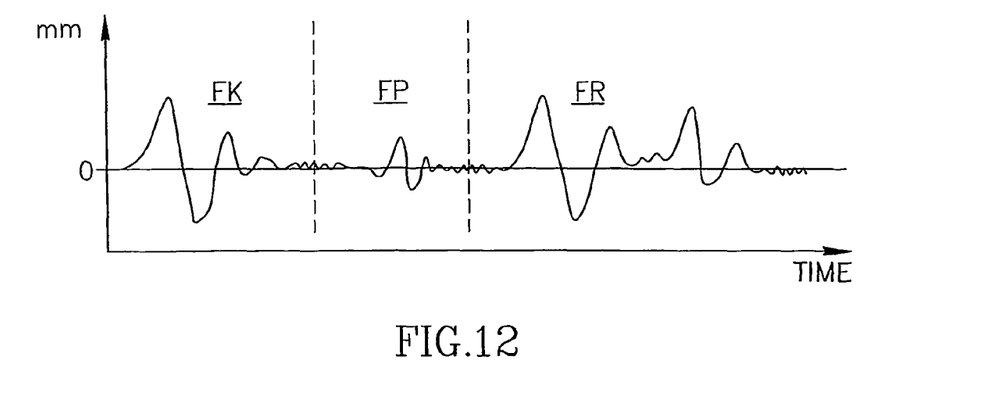
FIG. 12 is an exemplary graph of an expectant mother's abdomen's relative abdominal displacements in mm against time as sensed by a fetal motor activity sensor for a strong fetal kick FK followed by a weak fetal punch FP followed by a slow fetal roll FR.
Figure 13:
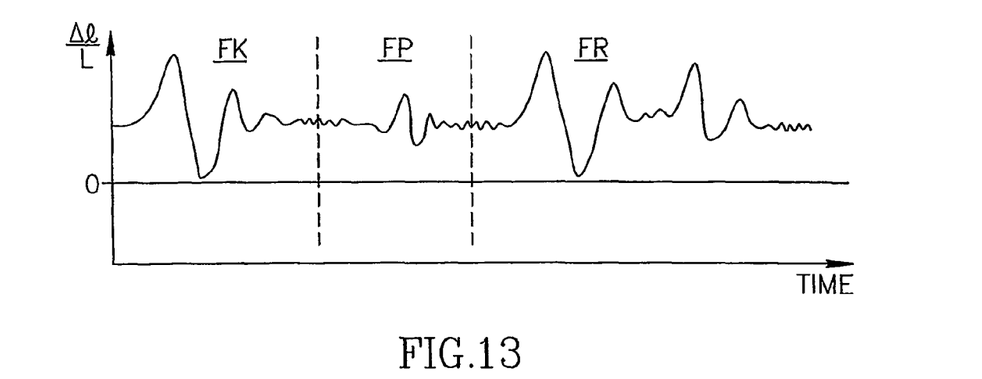
FIG. 13 is an exemplary graph showing strain developed by a fetal motor activity sensor in micro-strains against time corresponding to FIG. 12's fetal motor activities.
Figure 14:
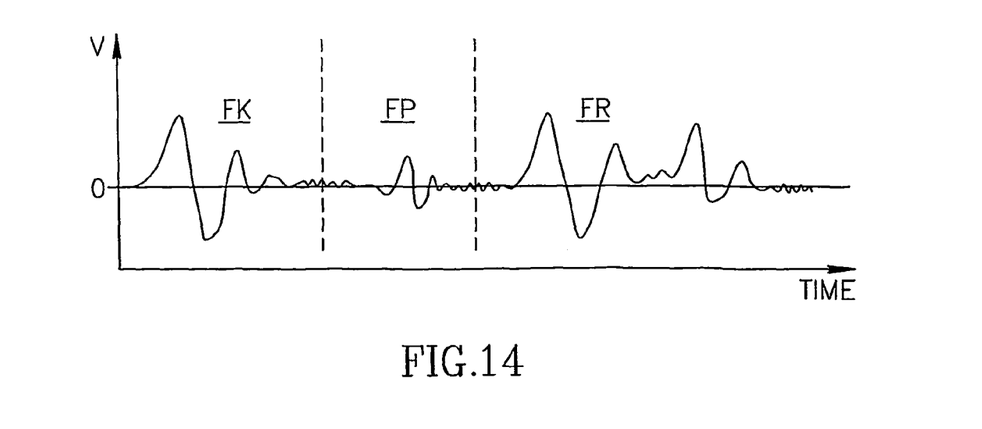
FIG. 14 is an exemplary graph showing time varying information in volts against time corresponding to FIG. 12's fetal motor activities.

FIGS. 12 to 14 show exemplary graphs of an expectant mother's abdomen's relative abdominal displacements in mm against time, the corresponding strain developed by a fetal motor activity sensor's strain gauge film element as a consequence of her relative abdominal displacements in micro-strains against time, and the corresponding information signal in volts against time after filtering out maternal breathing. The graphs depict a strong fetal kick denoted FK, for example, the strong fetal kick to the right denoted by the arrow P, followed by a weak fetal punch denoted FP followed by a slow fetal roll denoted FR. The nominal outward flexion of a strain gauge film element on a stationary expectant mother's abdomen leads to a DC like information signal which is typically offset such that the information signal is preferably zero irrespective of the degree of a nominal outward flexion.

Figure 15:
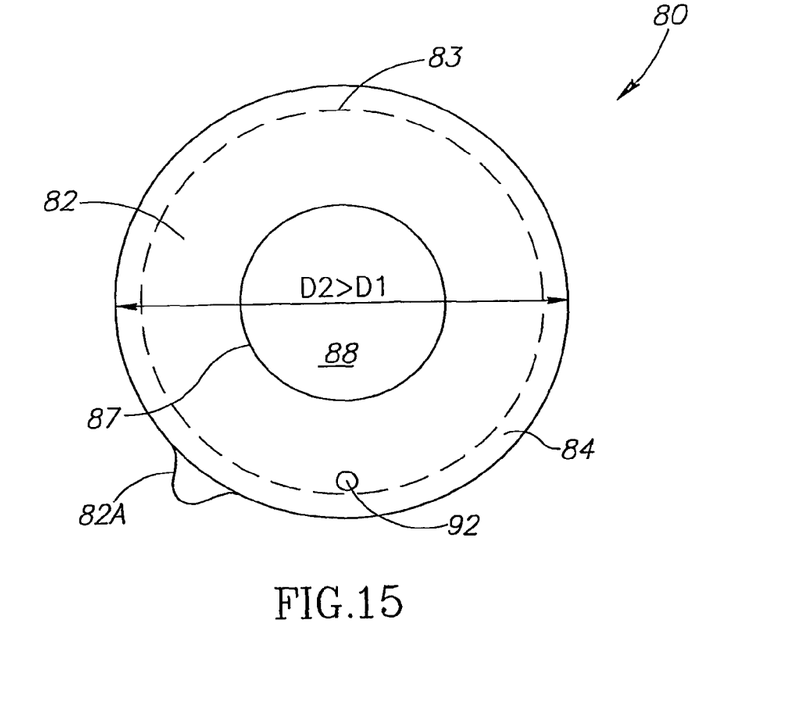
FIG. 15 is a top plan view of FIG. 1's pad.
Figure 16:
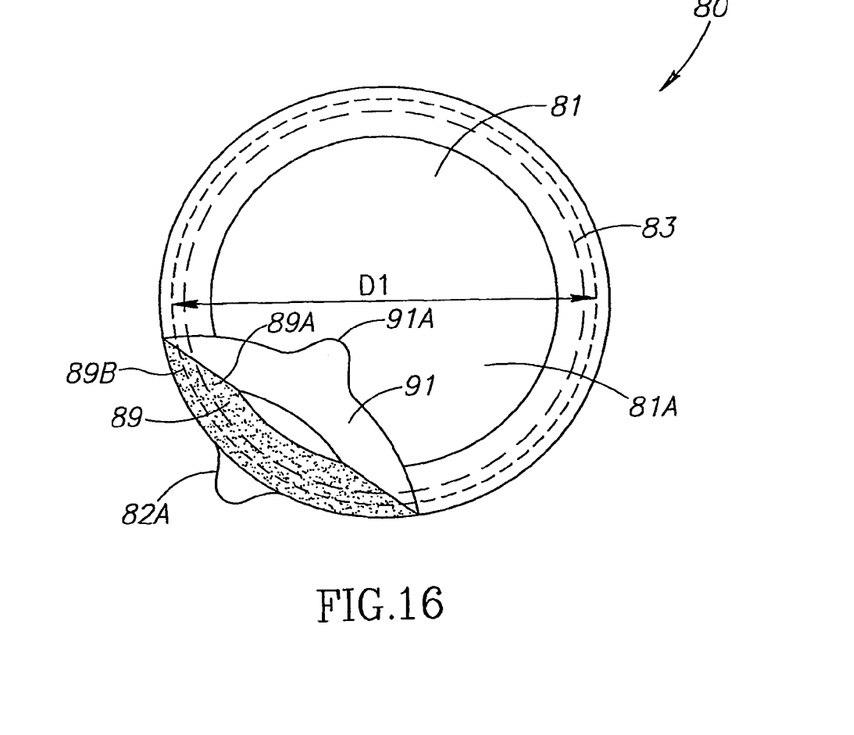
FIG. 16 is a bottom plan view of FIG. 1's pad.

FIGS. 15 and 16 show the two-ply pad 80 includes a generally circular base sheet 81 with a base sheet underside 81A, and a generally annular top sheet 82 joined to the base sheet 81 by a generally circular seam 83 having a diameter slightly greater than the housing's diameter. The base sheet 81 has an outer diameter D1 and the top sheet 82 has an outer diameter D2 where D2>D1 such that the top sheet 82 extends radially beyond the base sheet 81 in FIGS. 16's bottom plan view. The seam 83 can be stitched, ultrasound welded, glued, and the like. Both the base sheet 81 and the top sheet 82 are preferably formed from elastic non-woven fabric for attenuating high frequency noise. Suitable non-woven fabric includes Solastic NW PK6367.160, Nordenia International AG., Germany. The circular seam 83 delimits an annular rim 84.

Figure 17:
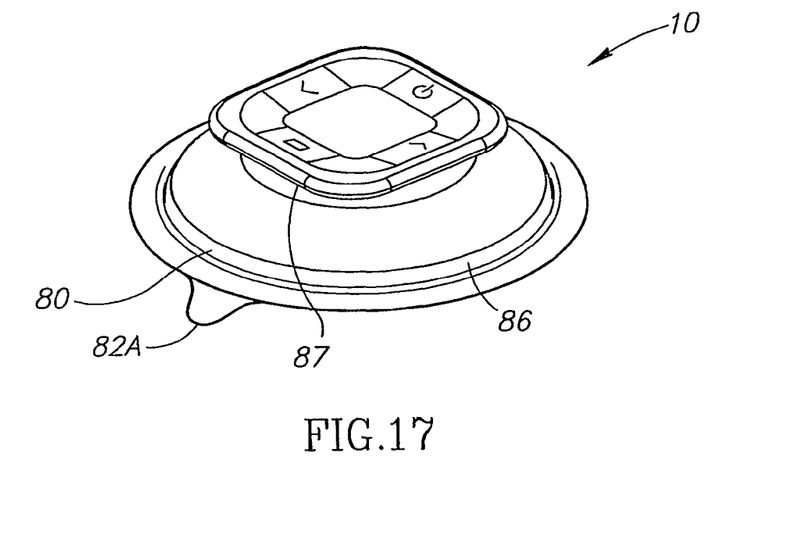
FIG. 17 is a perspective view showing FIG. 1's fetal wellbeing monitoring apparatus dressed in a pad.

The base sheet 81 and the top sheet 82 define a peripheral pocket 86 on dressing the pad 80 onto a fetal wellbeing monitoring apparatus 10 (see FIG. 17). The top sheet 82 has an internal rim 87 defining a central circular aperture 88 with a slightly greater cross section area than the turret-like user interface 16. The pad 80 is provided with an annular peripheral biocompatible adhesive surface 89 on the base sheet underside 81A for removable intimate adhesion on an expectant mother's abdomen. The adhesive surface 89 has a radial length of about 2 cm. The adhesive surface 89 preferably extends radial inwards from the top sheet's circumference for maximizing the moments for adhering the pad 80 to an expectant mother's abdomen. Suitable biocompatible adhesives are commercially available from 3M, Inc., US, for example, 3m 9874 Double Coated Medical Tape. The adhesive surface 89 is protected by a manually removable peel off protector 91 for exposing same. The seam 83 divides the adhesive surface 89 into a pair of concentric sections 89A and 89B of approximately equal radial length.

The top sheet 82 preferably includes a top sheet protruding tab 82A and the peel off protector 91 includes a protector protruding tab 91A underlying the top sheet protruding tab 82A for assisting removal of the peel off protector 91 for exposing the adhesive surface 89. The pad 80 can also include an aperture 92 for enabling access to a data port 62.

Figure 18:
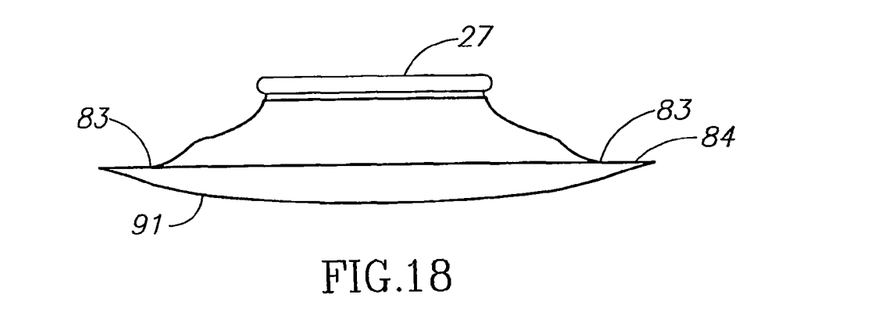
FIG. 18 is a side elevation view of FIG. 1's fetal wellbeing monitoring apparatus dressed in a pad.
Figure 19:
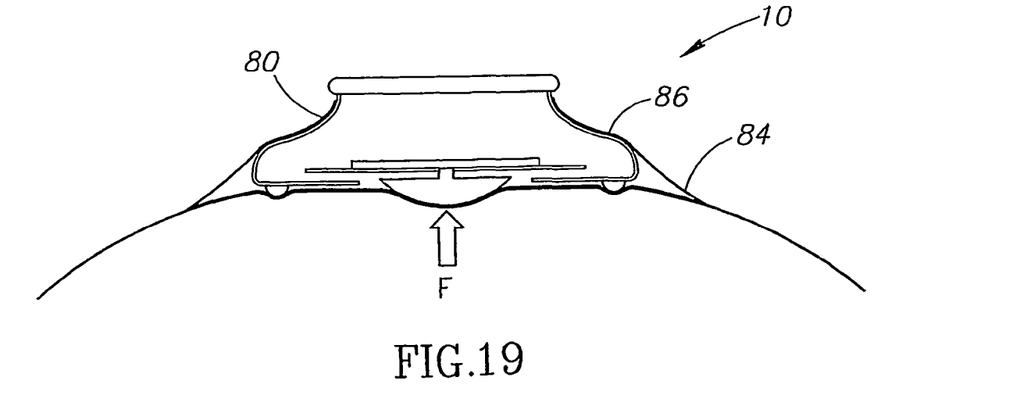
FIG. 19 is a cross section showing the action of FIG. 1's pad for intimately urging FIG. 1's fetal wellbeing monitoring apparatus against an expectant mother's abdomen.

FIGS. 17 and 18 show that dressing the pad 80 onto the fetal wellbeing monitoring apparatus 10 such that the turret-like user interface 16 uprightly protrudes through the pad's central aperture 88 causes the peripheral pocket 86 to be stretched onto the housing's peripheral portion 12 whereupon the rim 84 is upwardly turned by virtue of the elasticity of the top sheet 82. On removal of the peel off protector 91, an expectant mother outwardly and downwardly pulls on the rim 84 in the direction of the arrows D to adhere the pad 80 onto her abdomen whereupon the force F is applied against the fetal motor activity sensor 41 (see FIG. 19).

While the invention has been described with respect to a limited number of embodiments, it will be appreciated that many variations, modifications, and other applications of the invention can be made within the scope of the appended claims.

The invention claimed is:

1. A fetal wellbeing monitoring apparatus for providing fetal wellbeing information, the apparatus comprising:
    (a) a generally flattened hemispherical housing having an annular peripheral portion with an upright sloping topside and an annular flat underside defining a central sensor aperture for respectively facing away from and towards an expectant mother's abdomen,
    said housing including a fetal motor activity sensor with a rigidly mounted downward depending rounded contact protruding through said sensor aperture for indenting an expectant mother's abdomen on intimately juxtaposing said housing's underside thereagainst for sensing fetal motor activity; and
    (b) a turret-like user interface having a user operable control panel raised with respect to said housing's topside for controlling operation of the fetal wellbeing monitoring apparatus and providing fetal wellbeing information to the expectant mother.

2. The apparatus according to claim 1 wherein said user interface includes an illumination arrangement for providing illumination responsive to said fetal motor activity visible along a first line of sight directed toward said user interface from above and a second line of sight directed toward said user interface from a side direction.

3. The apparatus according to claim 2 wherein said illumination arrangement surrounds said control panel.

4. The apparatus according to claim 1 wherein said user interface includes a neck portion and an uppermost surface with a surround flared with respect to said neck portion for assisting manipulation of the apparatus.

5. The apparatus according to claim 1 wherein said control panel includes a central display screen for providing visual indications regarding the operation of the fetal wellbeing monitoring apparatus and a peripheral arrangement of pushbuttons surrounding said display screen for controlling operation of the fetal wellbeing monitoring apparatus.

6. The apparatus according to claim 1 wherein said housing's underside's annular peripheral portion includes a series of spaced apart rounded projections protruding less from said housing's underside than said fetal motor activity sensor's rounded contact to enable shear waves to travel across an expectant mother's abdomen.

7. The apparatus according to claim 1 and further comprising a loudspeaker for issuing a first set of operation sounds regarding operation of the fetal wellbeing monitoring apparatus and a second set of movement sounds different from said first set of operation sounds and responsive to fetal motor activity.

8. The apparatus according to claim 1 and further comprising a maternal body movement detection module for issuing an audible warning indicative of an expectant mother's body movement hindering fetal wellbeing monitoring.

9. The apparatus according to claim 1 and further comprising a non-magnetic loudspeaker for issuing sounds.

10. The apparatus according to claim 1 wherein said fetal motor activity sensor includes a base plate with a base plate topside and a base plate underside including said rounded contact for respectively facing away from and towards an expectant mother's abdomen, said base plate topside having at least one planar strain gauge film element defining a nominal measurement plane in a non-flexed state, and having a variable electrical property proportional to resilient elastic flexion in a transverse direction to said measurement plane on application of a bending moment, said at least one strain gauge film element configured to assume a nominal flexed state on intimate juxtapositioning against an expectant mother's abdomen in the absence of fetal motor activity, and further configured to flex in said transverse direction for inducing and induce corresponding changes in said variable electrical property when transient abdominal movements of the expectant mother's abdomen impart flexural movements onto said at least one strain gauge film element; and (c) a fetal motor activity determination module for processing time varying information from said fetal motor activity sensor to determine fetal motor activity and to provide fetal wellbeing information to the expectant mother.

11. The apparatus according to claim 10 wherein said base plate includes a pair of opposite elongated weakened regions for defining a major base plate surround supporting a minor base plate beam between a pair of beam supports for resilient elastic flexion relative to said major base plate surround and said minor base plate beam supports said at least one elongated planar strain gauge film element.

12. The apparatus according to claim 11 wherein said pair of opposite elongated weakened regions comprises a pair of throughgoing slits.

13. The apparatus according to claim 10 wherein said base plate topside has a pair of spaced apart planar strain gauge film elements for providing phase information regarding said transient abdominal movements.

14. A fetal wellbeing monitoring apparatus for providing fetal wellbeing information to an expectant mother, the apparatus comprising:

(a) a fetal motor activity sensor including a base plate with a base plate topside and a base plate underside for respectively facing away from and towards an expectant mother's abdomen, said base plate topside having at least one planar strain gauge film element defining a nominal measurement plane in a non-flexed state, and having a variable electrical property proportional to resilient elastic flexion in a transverse direction to said measurement plane on application of a bending moment, said base plate underside having a rigidly mounted downward depending protruding contact for indenting an expectant mother's abdomen on intimately juxtapositioning said base plate underside thereagainst, said at least one planar strain gauge film element configured to assume a nominal flexed state on intimate juxtapositioning against an expectant mother's abdomen in the absence of fetal motor activity, and further configured to flex in said transverse direction and induce corresponding changes in said variable electrical property when transient abdominal movements of the expectant mother's abdomen impart flexural movements onto said at least one strain gauge film element; and (b) a fetal motor activity determination module for processing time varying information from said fetal motor activity sensor to determine fetal motor activity and to provide fetal wellbeing information to the expectant mother;

wherein said base plate includes a pair of opposite elongated weakened regions for defining a major base plate surround supporting a minor base plate beam between a pair of opposite beam supports for resilient elastic flexion relative to said major base plate surround and said minor base plate beam supports said at least one elongated planar strain gauge film element.

15. The apparatus according to claim 14 wherein said pair of opposite elongated weakened regions comprises a pair of throughgoing slits.

16. The apparatus according to claim 14 wherein said base plate topside has a pair of spaced apart planar strain gauge film elements for providing phase information regarding said transient abdominal movements.

17. The apparatus according to claim 14 and further comprising:

(c) a generally flattened hemispherical housing having an annular peripheral portion with an upright sloping topside and an annular flat underside defining a central sensor aperture for respectively facing away from and towards the expectant mother's abdomen wherein said housing includes said fetal motor activity sensor with said rigidly mounted downward depending rounded contact protruding through said central sensor aperture, and (d) a turret-like user interface having a user operable control panel raised with respect to said housing's topside for controlling operation of the fetal wellbeing monitoring apparatus and providing fetal wellbeing information to the expectant mother.

18. The apparatus according to claim 17 wherein said user interface includes an illumination arrangement for providing illumination responsive to said fetal motor activity along a first line of sight directed toward said user interface from above and a second line of sight directed toward said user interface from a side direction.

19. The apparatus according to claim 18 wherein said illumination arrangement surrounds said control panel.

20. The apparatus according to claim 17 wherein said user interface includes a neck portion and an uppermost surface with a surround flared with respect to said neck portion for assisting manipulation of the apparatus.

21. The apparatus according to claim 17 wherein said control panel includes a central display screen for providing visual indications regarding operation of the fetal wellbeing monitoring apparatus and a peripheral arrangement of pushbuttons surrounding said display screen for controlling operation of the fetal wellbeing monitoring apparatus.

22. The apparatus according to claim 17 wherein said housing's underside's annular peripheral portion includes a series of spaced apart rounded projections protruding less from said housing's underside than said fetal motor activity sensor's rounded contact to enable shear waves to travel across an expectant mother's abdomen.

23. The apparatus according to claim 14 further comprising a loudspeaker for issuing a first set of operation sounds regarding operation of the fetal wellbeing monitoring apparatus and a second set of movement sounds different from said first set of operation sounds and responsive to fetal motor activity.

24. The apparatus according to claim 14 and further comprising a maternal body movement detection module for issuing an audible warning indicative of an expectant mother's body movement hindering fetal wellbeing monitoring.

25. The apparatus according to claim 14 and including a non-magnetic loudspeaker for issuing sounds.

26. A two-ply pad for use with a fetal wellbeing monitoring apparatus including a generally flattened hemispherical housing having an annular peripheral portion with an upright sloping topside and an annular flat underside defining a central sensor aperture for respectively facing away from and towards an expectant mother's abdomen, and a turret-like user interface having a user operable control panel raised with respect to the housing's topside for controlling operation of the fetal wellbeing monitoring apparatus and providing fetal wellbeing information to the expectant mother, the pad comprising:
  (a) a circular base sheet with an underside for intimate juxtapositioning against the expectant mother's abdomen, an annular top sheet overlying said base sheet, and a seam for attaching said top sheet to said bottom sheet, said top sheet having a central aperture whereby said top sheet and said base sheet define a pocket for stretchingly embracing the housing's peripheral portion with the underside of the base sheet facing towards the expectant mother's abdomen on dressing the pad onto the fetal wellbeing monitoring apparatus whereupon the control panel protrudes through said central aperture for enabling user access to the control panel's topside facing away from the expectant mother's abdomen; and
  (b) an annular peripheral biocompatible adhesive surface on at least said base sheet's underside for removable intimate adhesion of the pad on the expectant mother's abdomen.

27. The pad according to claim 26 wherein at least said top sheet is formed from elastic non-woven fabric.

28. The pad according to claim 26 wherein said top sheet has a larger external diameter than said base sheet whereby said top sheet extends radially beyond said base sheet and said adhesive surface extends radial inward from said top sheet's circumference.

29. The pad according to claim 26 wherein said seam divides said adhesive surface into a pair of concentric sections.

30. The pad according to claim 26 and further comprising a manually removable peel off protector for protecting said adhesive surface whereupon removing said peel off protector exposes said adhesive surface.

31. The pad according to claim 30 wherein said peel off protector includes a protector protruding tab for assisting removal of said peel off protector for exposing said adhesive surface.

32. The pad according to claim 31 wherein said top sheet includes a top sheet protruding tab overlying said protector protruding tab.

33. The pad according to claim 26 wherein the housing includes a data port and the pad further comprises an aperture for enabling access to the data port.

* * * * *